US011193892B2

(12) United States Patent
Clarke et al.

(10) Patent No.: US 11,193,892 B2
(45) Date of Patent: Dec. 7, 2021

(54) METHODS AND DEVICES FOR MEASURING THE LEVELS OF ANALYTES IN BODY FLUIDS (71) Applicant: Morgan Innovation & Technology Ltd., Petersfield (GB)

(72) Inventors: Susan Elizabeth Clarke, Petersfield (GB); Rebecca Louise Quest, Petersfield (GB); James Quest, Petersfield (GB); Patrick Martin Maguire, County Wexford (IE); Kathryn Laura Whitehead, Petersfield (GB)

(73) Assignee: Morgan Innovation & Technology Ltd., Petersfield (GB)

( * ) Notice: Subject to any disclaimer, the term of this patent is extended or adjusted under 35 U.S.C. 154(b) by 351 days.

(21) Appl. No.: 16/093,526

(22) PCT Filed: Apr. 13, 2017

(86) PCT No.: PCT/EP2017/059001
§ 371 (c)(1),
(2) Date: Oct. 12, 2018

(87) PCT Pub. No.: WO2017/178621
PCT Pub. Date: Oct. 19, 2017

(65) Prior Publication Data
US 2019/0128813 A1    May 2, 2019

(30) Foreign Application Priority Data
Apr. 14, 2016 (GB) .................................... 1606549

(51) Int. Cl.
*G01N 21/78* (2006.01)
*B01L 3/00* (2006.01)
*G01N 33/52* (2006.01)
*G01N 21/84* (2006.01)
*A61B 10/00* (2006.01)
*A61B 5/103* (2006.01)
*A61B 5/00* (2006.01)

(52) U.S. Cl.
CPC ........... *G01N 21/78* (2013.01); *A61B 5/1032* (2013.01); *A61B 5/4277* (2013.01); *A61B 5/4869* (2013.01); *A61B 10/0051* (2013.01); *B01L 3/5023* (2013.01); *G01N 21/8483* (2013.01); *G01N 33/523* (2013.01); *B01L 2300/043* (2013.01); *B01L 2300/047* (2013.01); *B01L 2300/069* (2013.01); *B01L 2300/123* (2013.01); *B01L 2300/161* (2013.01); *G01N 33/52* (2013.01)

(58) Field of Classification Search
CPC .. G01N 21/78; G01N 21/8483; G01N 33/523; A61B 5/1032; A61B 5/4277
See application file for complete search history.

(56) References Cited

U.S. PATENT DOCUMENTS

2003/0175993 A1  9/2003  Toranto et al.
2004/0171173 A1  9/2004  Eckermann et al.
2007/0020766 A1* 1/2007  Owen-Smith ...... G01N 33/6893 436/99
2009/0197296 A1* 8/2009  Martin .................... G01N 33/52 435/29
2009/0318829 A1* 12/2009  Hannant ............... B01L 3/5029 600/562
2012/0033064 A1  2/2012  Yamada et al.
2013/0267032 A1  10/2013  Tsai et al.
2015/0350605 A1  12/2015  Price et al.
2016/0080548 A1  3/2016  Erickson et al.
2017/0184506 A1* 6/2017  Patel .................... G01N 33/521

FOREIGN PATENT DOCUMENTS

| EP | 1160571 A1 | 12/2001 |
|---|---|---|
| EP | 3578959 A2 | 12/2019 |
| JP | 2001-337087 | 12/2001 |
| JP | 2003-532896 | 11/2003 |
| JP | 2004-534944 | 11/2004 |
| JP | 2004-537712 A | 12/2004 |
| JP | 2006-226865 | 8/2006 |
| JP | 2006-527847 | 12/2006 |
| JP | 2009-109384 A | 5/2009 |
| JP | 2011-196825 | 10/2011 |
| JP | 2012-037432 A | 2/2012 |
| JP | 2015-010943 | 1/2015 |
| JP | 2015-501929 | 1/2015 |
| JP | 2015-510118 | 4/2015 |
| JP | 2015-536465 | 12/2015 |
| WO | WO 2001/086292 A2 | 11/2001 |
| WO | WO 02/37944 A2 | 5/2002 |
| WO | WO 2004/113926 A2 | 12/2004 |
| WO | WO 2013/077802 A1 | 5/2013 |
| WO | WO 2013/119266 A1 | 8/2013 |
| WO | WO 2013149598 | 10/2013 |
| WO | WO 2015/040190 A1 | 3/2015 |

OTHER PUBLICATIONS

Examination Report issued in Japanese Patent Application No. 2019-520548 dated Dec. 10, 2019 (5 pages).
Kazuya, Miyanishi et al., "Statistics of Pregnancy Toxemia and Current State of Treatment Thereof in the Center" *Journal of Osaka Medical Center & Research Institute of Maternal and Child Health*, vol. 4, No. 1, pp. 1-5 (Mar. 1988).

(Continued)

Primary Examiner — Christopher Adam Hixson
(74) *Attorney, Agent, or Firm* — Finnegan, Henderson, Farabow, Garrett & Dunner, LLP (57) ABSTRACT

A method of testing for an analyte in an individual comprises providing colour information obtained from a digital image of a coloured reagent on an analyte test strip, the coloured reagent having been generated in accordance with analyte in a test sample, converting the colour information from the image into an analyte level, recording the analyte level in association with user-specific information (e.g. a QR code), repeating the above steps to obtain two or more records of analyte levels for the same user at different times and using the records to monitor personal health or to predict the likely development of a disease or condition or to diagnose a disease or condition or to monitor a treatment regime associated with variation in analyte levels in saliva.

16 Claims, 7 Drawing Sheets

(56) References Cited

OTHER PUBLICATIONS

Examination Report dated Sep. 8, 2020, issued in Japanese Patent Application No. 2018-554004 (7 pages).
International Search Report issued in International Application No. PCT/EP2017/059001 dated Dec. 15, 2017.
Written Opinion of International Searching Authority in International Application No. PCT/EP2017/059001 dated Dec. 15, 2017.
Official Action dated Mar. 16, 2021, in corresponding Japanese Application No. JP 2018-554004 (12 pages).

* cited by examiner

METHODS AND DEVICES FOR MEASURING THE LEVELS OF ANALYTES IN BODY FLUIDS

INTRODUCTION

The present invention relates to methods and devices for monitoring the levels of analytes, e.g. in saliva, in an individual, and in particular to a hand-held collection and testing device and related methods to quantify the levels of analytes and process the test results.

BACKGROUND TO THE INVENTION

Early detection of disease plays an important role in treatment planning and prognosis.

Saliva has great potential as a diagnostic fluid owing to the plethora of molecules present, such as hormones, proteins and salts, that can act as biomarkers for monitoring a physiological condition, predicting the likely development of a given disease or indeed diagnosing a disease. Correlations between salivary cortisol levels and diseases of the adrenal cortex have been noted as have correlations between salivary uric acid levels and both gout and pre-eclampsia. In fact, evidence suggests that elevated uric acid levels during pregnancy may not only be a valuable biomarker for pre-eclampsia, but also foetal distress.

Advantages of saliva as a clinical tool include the fact it can be collected non-invasively aiding patient cooperation, often only small quantities are needed for analysis and it can be easily stored and transported as regulatory agencies do not consider it to be a biohazard. Each of these aspects leads to a reduction in the cost associated with carrying out a diagnostic test. Additionally, the levels of many molecules in saliva have been found to correlate well with levels in the blood.

A variety of kits are available for measuring the levels of analytes in saliva. DiagnosTechs provide home test kits for measuring the levels of various hormones such as progesterone and estradiol in saliva samples. However, only the collection aspect is completed in the home and the user is required to spit into the collection vials provided in the kit. The saliva sample is then sent away to a laboratory and analysed by means of an ELISA which can take between 5-10 working days to complete before the results are dispatched to the user.

ZRT offers similar home test kits for saliva testing but again the kits involve the user spitting into a collection tube and sending the saliva sample away for analysis. Once the sample has been analysed, an evaluation report is dispatched to the user and/or healthcare provider within 5-7 working days meaning the test can take up to 10 days to complete in full. The time period between supplying the saliva sample and obtaining a result is a significant limitation of these saliva testing kits.

Testing kits that allow both collection and analysis in the home are available. U.S. Pat. No. 6,623,698 provides a saliva-monitoring biosensor electrical toothbrush that both collects and analyses the levels of various analytes in saliva. Vibrating bristles on the toothbrush head stimulate saliva secretion and accumulation into a test channel. When the test channel is filled with saliva, a channel cover moves across the opening of the channel to seal the channel. At that point, test reagents are released into the channel and after a predetermined period of time, sensors in the channel take readings on the optical density and/or the electrical current level which reflects the concentration of specific analytes in the saliva sample. A microprocessor inside the toothbrush handle compares the new data against established threshold values and a display unit on the toothbrush handle presents the data to the user. Whilst the device provides a means to measure various analytes in saliva, it is a complex piece of equipment and thus is expensive to both produce and buy. There is also a risk of contamination during testing if 1) the user has sensitive gums and a small amount of blood is drawn up into the test channel along with the saliva or 2) if the test channel is not cleaned out thoroughly enough between tests.

European Patent No. 1160571 provides test kits for use in detecting uric acid concentration in body fluid, which may be saliva. The detection method is based on the reduction of ammonium phosphotungstate by urate to produce a blue complex. The test kit is comprised of a test strip including a reagent portion and a means for determining the colour change of the reagent portion which may in the form of a colour card or a photometer. In the case of the colour card, the user would have to 'self-diagnose' which is a burden many users would not want. The described kit also doesn't provide a means for sample collection. For saliva testing, the user would have to drool onto the test strip which is unsightly and thus unappealing. There are also inherent problems with drooling onto the test strip, namely it is hard to direct the saliva onto the test reagents and it is difficult to control the volume of saliva expelled.

If only a small amount of saliva is expelled the first time the user drools onto the test strip, they may be encouraged to repeat the procedure which could affect the test readout.

Similarly to European Patent No. 1160571, CN102620953, WO2010/008989, WO2009/095826, WO2007/016866 and US2003/175993 provide test kits for detecting analyte levels in body fluids, which may be saliva, for use in the home. However, each relies on the user self-diagnosing which many users would not feel comfortable doing.

Thus there is a need for a saliva testing device that is simple, sensitive, inexpensive and provides a means for both collection and analysis of saliva in the home, preferably with involvement of a clinician.

Similarly there is a need in general for improved testing of analytes in other body fluids, especially so as to provide for simpler, home-based testing.

It is an aim of the current invention to provide an alternative device for saliva testing, especially an improved device. A related aim is to provide alternative methods and systems for capturing and processing test data, to provide information useful in monitoring personal health and diagnostics. Related aims are to provide alternative, preferably improved, methods and devices for body fluid analysis in general.

SUMMARY OF THE INVENTION

Accordingly, the invention provides a method of testing for an analyte in an individual, comprising:
 providing colour information obtained from a digital image of a coloured reagent on an analyte test strip, the coloured reagent having been generated in accordance with analyte in a test sample,
 converting the colour information from the image into an analyte level, recording the analyte level in association with user-specific information (e.g. a QR code),
 repeating the above steps to obtain two or more records of analyte levels for the same user at different times, and using the records to monitor personal health or to predict the likely development of a disease or condition or to diagnose a disease or condition or to monitor a treatment regime associated with variation in analyte levels in saliva.

The invention further provides a device, optionally used in combination with the above method, for testing the level of an analyte in a saliva sample, comprising:— a first arm, on which is mounted a pad of absorbent material, and a second arm, which comprises a test strip, wherein the test strip comprises a reagent portion comprising an indicator capable of changing colour in accordance with the presence of an analyte, wherein the arms are connected by a hinge and can be pivoted on the hinge to bring the pad into contact with the reagent portion.

A further method of the invention, optionally used in combination with the above device and method, for testing for an analyte in an individual, comprising:—

(a) providing (i) a saliva sample from an individual in a pad of absorbent material, spaced from (ii) a test strip containing an indicator which is capable of generating a colour change in accordance with the presence of an analyte, (b) bringing the pad into contact with the test strip and holding the pad in contact with the test strip for sufficient time for saliva in the pad to be combined with the indicator and generate a colour in accordance with the level of an analyte if present, and (c) determining a level of analyte based upon the colour change.

The device and methods are suitably applied in monitoring personal health or predicting the likely development of a disease or diagnosis of a disease or condition associated with variation in the levels of analytes present in saliva or in monitoring a treatment regime associated with variation in the levels of analytes present in saliva.

DETAILS OF THE INVENTION

As described herein, also with optional and preferred features and in three specific embodiments detailed below, a device of the invention for testing the levels of a salivary analyte, comprises:— a first arm, on which is mounted a pad of absorbent material, and a second arm, which comprises a test strip, wherein the test strip comprises a reagent portion comprising an indicator capable of changing colour in accordance with the presence of an analyte, wherein the arms are connected by a hinge and can be pivoted on the hinge to bring the pad into contact with the reagent portion.

This enables a reaction between the saliva in the pad and the chemical reagent(s) in the reagent portion. Typically, the arms are connected by a hinge and can be pivoted or rotated on the hinge to bring the pad into contact with the reagent portion.

The pad, which in use is soaked with saliva, and the reagent portion are hence separated in space and only brought together when the user determines there is sufficient saliva volume to perform a test. Carrying out the test may require contact time to be measured, in which case the arms can be kept apart and then contact can be effected once the user has the timer ready. In use of devices described elsewhere herein, contact times of the order of 1 to 20 seconds have worked, and about 3-5 seconds in some specific examples.

In preferred devices movement about the hinge is restricted such that when the two arms are rotated towards each other the pad inevitably makes contact with the reagent portion. This makes the device easy-to-use and helps reduce patient error when testing. In general, the device is flat and elongated, and is hinged dividing the device into two segments which in some embodiments are equal in length but in others are asymmetrical. The two segments fold together to form a cohesive, single unit and are easily held together by a single hand.

The second arm may comprise a translucent window, with the test strip located on a front surface of the second arm in alignment with the window. The colour change in the reagent portion is then visible from the rear surface of the second arm, through the window; hence, inspection of the colour can take place without having to reopen the folded device. The window is preferably substantially transparent, and clear plastics and glass are suitable materials. The second arm may also be made of translucent, preferably substantially transparent, material, allowing inspection from the rear.

In preferred embodiments, the test strip is thin and flat. It is usually substantially planar. Especially suitable are strips of thickness up to approximately 0.5 mm, preferably up to approximately 0.3 mm. In examples where we have tested the concentration of urate in saliva we have used strips approximately 0.15 mm thick, and have found that the colour generated, by newly formed chemicals in the strip material, is visible rapidly on all faces of the test strip; hence making the test strip colour output quickly and readily readable from the front (meaning the surface making contact with the pad) or rear (e.g. through the optional window, or when the second arm is translucent or transparent). Absorbent paper, e.g. cellulose filter paper, has been used for the strip, though the material is not critical. The chemistry of the reagent is dealt with elsewhere but, again, is not critical provided a colour change occurs that correlates with the concentration of a given analyte present in saliva. In this context, colour change includes detectable colour generation, colour gain and colour loss. The test strip can be of various dimensions; the device of embodiment 1 described below has a test strip approximately 10 mm×5 mm, i.e. 50 $mm^2$ in area and the device of embodiments 2 and 3 described below has a test strip of approximately 10 mm×10 mm, i.e. 100 $m^2$.

The pad is in general made of any suitable, absorbent material. In use we have found good results with resilient foams, preferably hydrophilic foam. The material should absorb saliva and release it when pressed against the reagent portion. Open cell foams are also preferred, and small cell foams in particular. In embodiment 1 described in more detail below, Capu-Cell® medium density foam was used. This is a semi-closed cell (i.e. partially open cell), hydrophilic, urethane foam. In embodiments 2 and 3 described in more detail below, PureSorb™ Foam Wiper was used. This is a hydrophilic polyurethane foam.

It is also preferred that the pad is not too large and/or that the volume of saliva it holds is not too great. Prior art tests have failed due to a high saliva volume requirement, and the invention seeks to avoid that and related problems. Suitably, the front surface of the pad has an area of up to approximately 600 $mm^2$, more suitably an area of up to approximately 500 $mm^2$, more suitably an area of up to approximately 400 $mm^2$ or 300 $mm^2$. The device of embodiment 1 has a pad 10 mm×20 mm, i.e. 200 $mm^2$ in area. The device of embodiments 2 and 3 described in more detail below has a hexagonal pad of between 200-300 $mm^2$ in area. It is preferred that the pad has a limited volume, especially of up to approximately 1000 µl, or up to approximately 500 µl, preferably up to 350 µl, more preferably up to 250 µl or up to 200 µl. Smaller pads have, we find, produced better patient compliance and more reliable testing with fewer failed tests. In tests, some bigger pads, approximately 400 µl pads have been used successfully. Separately, the pad should have a minimum volume, optionally a minimum volume of about 50-100 µl.

The pad may be replaceable. The pad may be releasably attached to the first arm of the device or alternatively the first arm may comprise a detachable head portion comprising the pad. In example 1 described in more detail below the head portion comprising the pad is replaced with each use.

The device may comprise a clip or lock arrangement, optionally releasable, engaged when the first and second arms are brought into contact and capable of holding the arms together with the pad pressed onto the reagent portion. Once the pad is touching the reagent portion the clip can be used to retain it there, e.g. while the user is counting the reaction time until the colour is ready to be assessed. The clip typically can be released to separate the pad from the reagent portion to allow inspection of the reagent portion from the front. When there is a window, or the second arm is translucent or transparent, this is not needed as inspection from the rear is possible.

Improved results are obtained with attention to the respective sizes of the pad and reagent portion on the test strip. Hence, in preferred embodiments the respective pad and reagent portion dimensions are such that the arms can be pivoted on the hinge to bring the entire front surface of the reagent portion into contact with the pad. This ensures that substantially all the reagents in the reagent portion come directly into contact with the saliva—the saliva does not to any significant extent flow laterally through the material of the reagent portion but flows into it orthogonally to the plane of the test strip.

Further preferred is that the pad front surface area is at least slightly greater than that of the reagent portion, and wherein the arms can be pivoted on the hinge to bring the pad into contact with the reagent portion with the front face of the pad in contact with and surrounding the reagent portion.

More preferred are devices wherein the pad dimensions are greater in height and width than those of the reagent portion such that its front surface area is greater than that of the reagent portion, and wherein the arms can be pivoted on the hinge to bring the pad into contact with the reagent portion with a peripheral region of the front of the pad surrounding the reagent portion of the test strip. The pad material is resilient and hence when pressed against a thin test strip, mounted in a shallow channel (e.g. incorporated into the second arm or incorporated in a cassette which is inserted into a receiving socket on the second arm) or on and thus in line with or slightly proud of a substantially flat device surface, inner portions of the front pad surface will be compressed whereas pad material in the periphery will be less or non-compressed and therefore will contact the device surface surrounding the test strip. This is shown in a first specific embodiment of the example. In the first embodiment of the example the pad and test strip are both rectangular but the shape is not critical in this respect, provided the pad can surround the reagent portion of the test strip (whatever is the shape). For example, round or oval shaped pads and reagent portions or hexagonal pads are also suitable. The "surrounding" engagement of the reagent portion by the saliva-containing pad aids reliable and error free tests.

The device suitably comprises a colour calibration icon e.g. a CMYK (Cyan, Magenta, Yellow and Black) icon adjacent to the test strip. When there is a window, or the second arm is translucent or transparent, the colour calibration icon can be seen from the reverse of the second arm of the device. Having the colour calibration icon present means that an image of the coloured reagent on the test strip next to the colour calibration icon can be assessed, making it possible to allow for different lighting conditions and reduce error or other variation caused thereby. If a camera e.g. on a smartphone is used, optionally with a flash, the image captured may thus include the colour newly generated from the test next to the colour calibration icon for comparison purposes. The device may separately or additionally also comprise one or more pre-printed colour standards indicative of different analyte (e.g. urate) levels, located adjacent to the test strip. Assessing the test then comprises assessing the colour change next to the one or more standards. When there is a window, or the second arm is translucent or transparent the colour standards can be seen from the reverse of the second arm of the device.

In one series of devices made to test the levels of uric acid in saliva samples three colour standards are provided, indicative of respectively low, medium and high levels of uric acid in saliva.

The device suitably comprises a user identifier e.g. a QR code. When there is a window, or the second arm is translucent or transparent the user-identifier can be seen from the reverse of the second arm of the device. Having the user-identifier means that when the coloured reagent on the test strip is analysed by means of obtaining a digital image of the test strip and sending it to a remote monitoring station for analysis, the test result can be saved along with the user-identifier. Notably the user-identifier preferably contains no personal information thus the image can be sent to the remote monitoring station confidentially.

The chemistry of the reagent making up the test strip is not specifically a feature of the invention. It is nevertheless preferred that the indicator is capable of generating a colour change in accordance with the concentration of a given analyte present in saliva. Specific examples of chemistry suitable for use in the invention are described in U.S. Pat. No. 6,699,720.

In specific, preferred examples of the invention, the device is portable and hand-held. This makes the device easy to use in the home. In a first specific embodiment, described in more detail in the example below, a device is provided wherein the pad is made of resilient, hydrophilic foam and has a volume of up to approximately 600 µl, wherein the pad dimensions are greater in height and width than those of the reagent portion such that its front surface area is greater than that of the reagent portion and wherein the arms can be pivoted on the hinge to bring the pad into contact with the reagent portion with a peripheral region of the front of the pad surrounding the reagent portion of the test strip, and wherein the device is flat and elongated, and hinged dividing the device into two segments and wherein movement about the hinge is restricted such that when the two segments are rotated towards each other the pad inevitably makes contact with the reagent portion.

Also provided by the invention are testing methods, optionally using the device. A method of testing for a given analyte in a sample of saliva thus comprises:—

(a) providing (i) a saliva sample in a pad of absorbent material, spaced from (ii) a test strip containing an indicator which is capable of generating a colour change in accordance with the presence of a given analyte, (b) bringing the pad into contact with the test strip and holding the pad in contact with the test strip for sufficient time for saliva in the pad to be combined with the indicator and generate a colour change in accordance with the concentration of a given analyte, and (c) determining a level of a given analyte based upon the colour change.

The method can be used in various monitoring and diagnostic applications. Typical methods comprise storing multiple test results for the same user taken at different times and comparing these to monitor personal health or predict the likely development of a condition or monitor a treatment regime associated with variation in the levels of a given analyte present in saliva or diagnose a disease or condition. By way of an example, if the analyte is uric acid then the methods can be used to diagnose foetal distress, predict the likely development of pre-eclampsia or to monitor patient response to therapy, e.g. therapy for gout.

In relation to predicting the likely development of pre-eclampsia, one clinically significant event is a high uric acid level, especially repeated high uric acid level readings after a period of medium or low readings. Use of the method with repeated tests enables monitoring of such variation in uric acid levels. In relation to treatment monitoring, taking gout therapy as an example, treatment to lower uric acid levels can have different effects in different patients and a quick and easy test that can be performed at home enables patients to self-test. If the medication administered needs to be increased or lowered this will be apparent from the results of repeated tests.

Thus in preferred embodiments of the invention the methods comprise transmitting information concerning the level of a given analyte present in saliva to a monitoring station at a remote site. Suitably, the information transmitted comprises colour information contained in or obtained from an image of the colour change on the test strip. A simple picture of the reagent portion taken with a camera, e.g. a smartphone camera, can be transmitted electronically, say by email or messaging service to the remote monitoring station.

The assessment of the concentration of a given analyte present in saliva preferably comprises determining the level based upon luminance, saturation or both luminance and saturation of the colour. This is better performed where the facilities exist, i.e. remotely from the user's typical home test location. Comparing multiple test results to identify incidence of a particular reading is preferred and facilitated by the combination of a method that can be performed locally and analysis that can be carried out remotely once digital information of the test has been transmitted.

Testing methods of the invention are preferably carried out using a device of the present invention. These methods thus comprise carrying out the test using a device comprising:—

(a) a first arm, on which is mounted a pad of absorbent material, and (b) a second arm, which comprises a test strip, wherein the test strip comprises a reagent portion comprising an indicator capable of changing colour in accordance with the presence of an analyte, wherein the arms are connected by a hinge and can be pivoted on the hinge to bring the pad into contact with the reagent portion.

As described elsewhere, the second arm may comprise a transparent window, the test strip may be located on a front surface of the second arm either in line with or slightly proud of the surface of the second arm or in a shallow channel which may be incorporated into the second arm or may be held in a cassette which is inserted into a receiving socket within the second arm and the colour generated in the reagent portion may be visible from the rear surface through the window, and the method may then comprise inspecting the colour through the window.

In embodiments, the pad comprises hydrophilic, resilient foam, the pad front surface area is at least slightly greater than that of the reagent portion, and the method comprises pivoting the arms to bring the pad into contact with the reagent portion with the front of the pad in contact with and surrounding the reagent portion.

The device can comprise an optionally releasable clip or lock arrangement, capable of holding the arms together with the pad pressed onto the reagent portion; the method may comprise bringing the first and second arms together until the clip engages and holds the arms together. The device can be flat and elongated, and hinged dividing the device into two segments with movement about the hinge restricted such that when the two segments are rotated towards each other the pad inevitably makes contact with the reagent portion. The second arm of the device may comprise one or more pre-printed colour standards indicative of different levels of a given analyte present in saliva, located adjacent to the test strip. The second arm may also comprise a colour calibration icon e.g. a CMYK icon and/or a user-identifier. When the device comprises the window the method may comprise obtaining an image of the colour through the window. If the device comprises a colour calibration icon and/or a user-identifier, the method may comprise obtaining an image of the colour reagent in combination with the colour calibration icon and/or user-identifier through the window.

A related method, optionally for use in combination with the above user test methods and/or devices, carries out the colour analysis. This method may be performed by a computer programmed accordingly, and may optionally be performed by a combination of a computer in one location, especially such as a smartphone, and a remotely located second device, typically comprising a computer.

Such a method of testing the levels of a given analyte in a sample of saliva comprises:

providing colour information obtained from a digital image of a coloured reagent on an analyte test strip, the coloured reagent having been generated in accordance with analyte in a test sample, converting the colour information from the image into an analyte level, recording the analyte level in association with user-specific information (e.g. a QR code), repeating the above steps to obtain two or more records of analyte levels for the same user at different times, and using the records to monitor personal health or to predict the likely development of a disease or condition or to diagnose a disease or condition or to monitor a treatment regime associated with variation in analyte levels in saliva Preferably, the method comprises obtaining two or more records, more preferably three or more, more preferably 5 or more records, of the concentration of a given analyte for the same user at different test times. This enables monitoring of a trend in analyte level over time.

Colour information is readily obtained using a digital camera, especially a camera on a smartphone. Data in the digital image, i.e. colour information, can be processed by the smartphone, e.g. using an app, generating an analyte measurement directly. Alternatively, data can be transmitted, optionally via an app run on the user's smartphone, for remote processing. Preferred methods comprise capturing a digital image of the test strip post test (e.g. via taking a photograph of the coloured reagent on the analyte test strip using a smartphone), transmitting the digital image to a monitoring station at a second, remote site, and converting the colour information into a reading, such as concentration, at the monitoring station. This avoids errors in data processing by smartphones that not have been updated. The digital image may be processed to obtain the colour information or the colour information may be obtained directly from the digital image.

In embodiments the method is performed by a program run on a hand-held computing device, especially on a smartphone, which program we will refer to as an app. The app, once invoked, can include various other steps, such as one or more or all of:—
1. counting a suitable interval for the pad to be in contact with the reagent portion and sounding an alarm once the interval has expired;
2. assessing whether the hand-held device camera is suitably distanced from the reagent portion, i.e. not too close and not too far;
3. ensuring the lighting conditions are within acceptable boundaries, e.g. switching on the flash to capture the image;
4. identifying a surface or other feature on the reagent portion or test strip or testing device that confirms an image of a reagent portion is about to be captured;
5. identifying a region in the image that contains the colour information or from which the colour information can be derived;
6. linking that colour information with a user identifier;
7. transmitting colour information in association with user identifier information to a remote monitoring station.

A specific method of the invention for testing the level of a given analyte in saliva operate using an app as follows. The user invokes the app and the app waits for an input to indicate the user wishes to carry out a test. If the device contains a user-identifier e.g. a QR code, the input may be a successful reading of the user-identifier. Once this has been completed the app directs the user to place the pad comprising portion of the first arm of the device into her/his mouth. Upon user-input, a timer begins and upon expiry of the pre-determined time limit, usually 30 seconds, the app issues an instruction to the user to remove the pad from her/his mouth and close the device such that the saliva containing pad comes into contact with the test strip.

Upon user-input, a time begins and upon expiry of the pre-determined time limit, usually 3-5 seconds, the app issues an instruction to the user to open the device. At this point the camera view appears and the app instructs the user to place the camera over the coloured reagent on the test strip such that the test strip, and when present the user-identifier and/or colour calibration icon, can be seen. The app then instructs the user to take a photograph. Once the photograph has been taken, the app transmits it to a remote monitoring station (also referred to as the distal site) where the colour information is converted into an analyte level. Other intermediate steps may also be included, such as prompts to the user to repeat a step that appears to have failed. The saliva sample is preferably obtained using a device that comprises a user identifier and/or a colour calibration icon such that these can be included in the digital image of the test strip. The program may also carry out an intermediate step of processing the image to ensure it meets predetermined criteria for a successful test, e.g. a colour has been generated and user identity information can be read from the image. If the image fails this step, the program may direct a retest.

To determine the concentration of the analyte, the method may do so based upon luminance, saturation or both luminance and saturation of the colour. Data obtained from clinical trials enables a look-up table to be pre-populated, so incoming results can be immediately converted into a level. The level can be reported in binary e.g. yes/no, semi-quantitative e.g. low, medium and high or quantitative format based on the assay characteristics. Alternatively, the outcome may be reported in more than one way i.e the absolute measurement and the band the absolute measurement falls into. As with the user methods, the analysis typically comprises storing and comparing multiple test results, e.g. at least 5 test results taken at different times for the same user. An obvious advantage of the above method is that the diagnosis is performed with input from clinicians, albeit indirectly.

Typically, a digital image is received via the app and pre-processed to remove data noise. Colour space feature extraction is then performed. Various colour models can be used including HSV (Hue, Saluration, Value), L*A*B (Luminance (L) and two colour channels (a & b), YCbCr (Luma component (Y) and chrominance-blue (Cb) and chrominance red (Cr)) and CIE 1931. The results of the colour space feature extraction are plotted on a feature space plot pre-populated with data points derived from images taken during clinical trials that have been linked with specific analyte levels. The analyte levels may have been grouped into categories such as low, medium or high. A k-nearest neighbors algorithm (k-NN) is then used to classify the sample. Once the sample has been classified, the result is stored, alongside the user-identifier, and the date and time. A trending algorithm monitors for instances of increased analyte levels. Should an instance arise, the monitoring platform sends an alert to a clinician who can link the user-identifier with a patient using patient records and act in accordance with general practice.

Further particular methods of the invention for testing the level of a given analyte in saliva comprise proximal and distal steps as set out below, yielding an assessment of analyte level useful in diagnosis, and preferably generating an alert if analyte levels over time meet the alert criteria, e.g. indicating a patient at risk. The steps include:
providing colour information obtained from a digital image of the test strip, once a colour change has occurred in response to the concentration of an analyte in the saliva sample,
converting the colour information from the digital image into a concentration,
storing a new record of concentration at a test time and if a previous record has been stored combining the new record with the previously stored record or records into a set of two or more records and
using the records to predict a physiological condition or the likelihood of a given disease developing or to diagnose a disease or condition or to monitor a treatment regime associated with variation in the levels of an analyte present in saliva.

The digital image is conveniently acquired proximally to the patient and preferably by the patient him- or herself, such as by taking a digital photograph of the test strip. A computer program running on a proximal device, e.g. a smartphone or computer (including laptops, desktops, tablets etc) may advantageously be used to capture the digital image and send the digital image or colour information to a distal site.

Processing of the colour information, e.g. converting the colour information into an analyte concentration, is conveniently carried out distally.

When the program is used, the user may start or otherwise invoke the program and the program waits for an input to indicate the user wishes to carry out a test. After receiving a positive input the program runs a timer for a predetermined period of time and on expiry issues an alert that the time period has expired. During this period, the user is intended to be obtaining a saliva sample. The program then waits for a further input to indicate the user wishes to proceed to the next part of the test. After receiving a positive input the program runs a second timer for a second predetermined period of time and on expiry issues an alert that the time period has expired. During this period the user is intended to be transferring the saliva sample to the test strip (so that a colour change may occur in response to analyte in the sample). The program then waits for a further input to indicate a digital image of the test strip may be captured and captures an image once a positive input is received. The user is intended to arrange a camera in a suitable position to capture a test strip image, including where present user specific information and, again where present, colour reference information—it being preferred that a single digital image include at least the test strip and the user identifier and more preferably the colour reference too. The program captures the image and transmits it to a remote location (also referred to as the distal site) for processing. Other intermediate steps may also be included, such as an explicit indication to the user as to the action he or she is intended to be taking at any given time and prompting to repeat a step that appears to have failed. The saliva sample is preferably obtained using a device that comprises a user identifier and/or a colour reference such that these can be included in the digital image of the test strip.

The program may carry out an intermediate step of processing the image to ensure it meets predetermined criteria for a successful test, e.g. a colour has been generated and user identifies information can be read from the image. If the image fails this step the program may direct a retest.

Processing at the distal site preferably comprises classifying the test according to a predetermined series of possible test outcomes and storing each outcome in association with user identifier information and time information so that test results for the same user at different times can be used for monitoring purposes. Presence of the colour reference in the digital image assists the classification. Typically, the outcomes are concentration levels of analyte, for example in one of two bands: e.g. high or low concentration, or one of three bands: e.g. high, medium or low concentration. There may be a greater number of bands. They may be given labels such as risk band, low risk band and similar, to assist the clinician's use of the results. The outcome may include the absolute measurement and also its classification into a band.

This distal processing preferably comprises noting receipt of the digital image and carrying out a step of confirming the image includes colour information (e.g. to confirm a test has been carried out) and user identifier information; generally, with no user identifier the image cannot be used and is rejected. The processing preferably comprises determining the analyte concentration, storing this in association with the user identifying information and reviewing the different concentrations for the same user at different time points and carrying out a diagnosis step based thereon. The diagnosis suitably determines if an alert is to be generated. In specific embodiments an algorithm is applied to the results to determine whether an alert, and if so which alert, should be generated.

The alert is then generally directed at a clinician, including the user identifier information. The clinician can use the identifier information to link the alert to a patient, typically via patient records, and process the patient alert in accordance with the local clinic practice. At the distal processing site it is preferred that there is insufficient data to connect the user identifier with the patient, hence maintaining patient confidentiality at the distal processing site.

In a further, related aspect, the invention extends more generally to testing of analyte levels in body fluids; these may include for example blood, serum, urine and saliva. Accordingly, the invention also provides a device for testing the levels of an analyte in a body fluid sample, comprising:—
  a first arm, on which is mounted a pad of absorbent material, and
  a second arm, which comprises a test strip, wherein the test strip comprises a reagent portion comprising an indicator capable of changing colour in accordance with the presence of an analyte,
  wherein the arms are connected by a hinge and can be pivoted on the hinge to bring the pad into contact with the reagent portion.

A method of this aspect of the invention, which optionally uses the above device, for testing the levels of an analyte in a body fluid sample, comprises:—
  (a) providing (i) a body fluid sample in a pad of absorbent material, spaced from (ii) a test strip containing an indicator which is capable of generating a colour change in accordance with the presence of a given analyte,
  (b) bringing the pad into contact with the test strip and holding the pad in contact with the test strip for sufficient time for the body fluid in the pad to be combined with the indicator and generate a colour change in accordance with the presence of a given analyte, and
  (c) determining the level of a given analyte in the body fluid based upon the colour change.

A further method of this aspect of the invention for testing the level of a given analyte in a body fluid, optionally using the information generated from the above method comprises:—
  providing colour information obtained from a digital image of a coloured reagent on an analyte test strip, the coloured reagent having been generated in accordance with analyte in a test sample,
  converting the colour information from the image into an analyte level,
  recording the analyte level in association with user-specific information (e.g. a QR code),
  repeating the above steps to obtain two or more records of analyte levels for the same user at different times, and
  using the records to monitor personal health or to predict the likely development of a disease or condition or to diagnose a disease or condition or to monitor a treatment regime associated with variation in the levels of an analyte present in body fluid.

The device and methods are suitably applied in monitoring personal health or predicting the likely development of a disease or diagnosis of a disease or condition associated with variation in the levels of analytes present in body fluid or in monitoring a treatment regime associated with variation in the levels of analytes present in body fluid.

Optional and preferred features of the invention in relation to testing of saliva provide corresponding optional and preferred features of the immediately above aspect relating to testing in general of body fluids.

DESCRIPTION OF FIGURES

The invention is now described in more detail with reference to specific embodiments and to the accompanying drawings, in which:—

Figure 1:
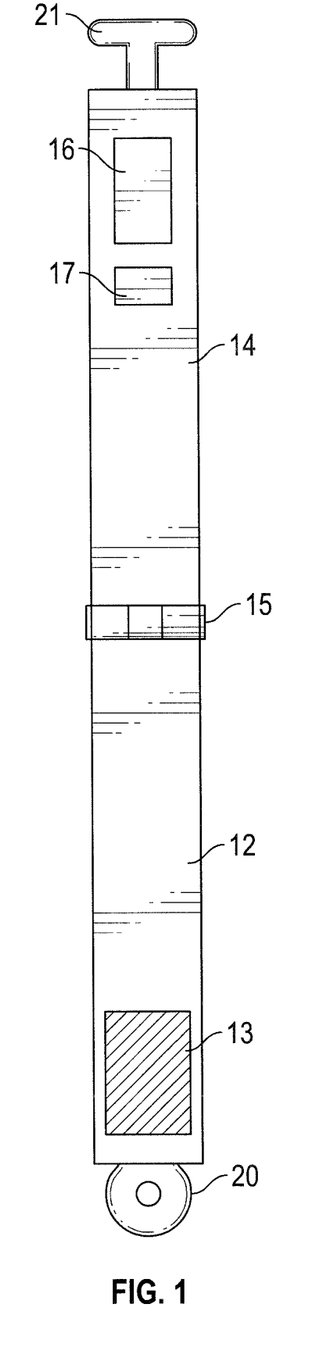
FIG. 1 is a schematic view of the front of a first device of the invention.
Figure 2:
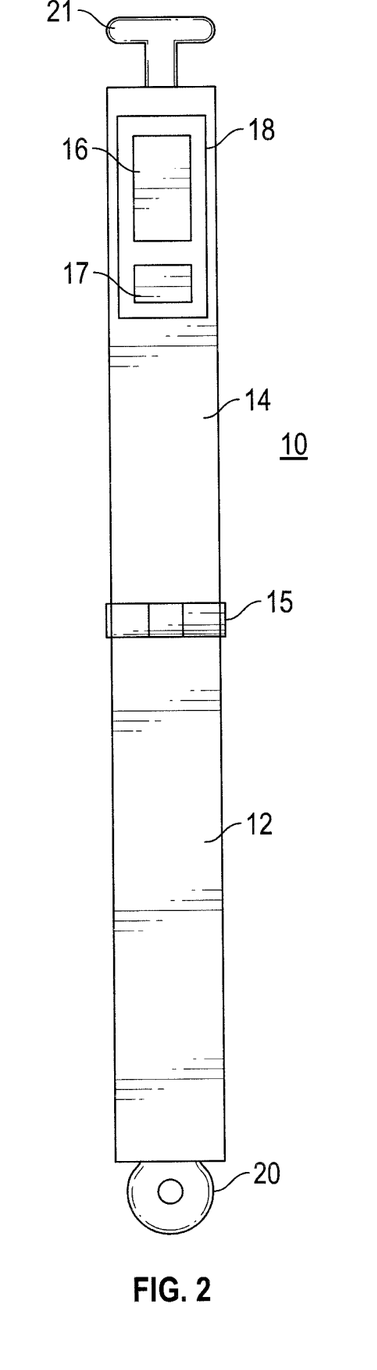
FIG. 2 is a schematic view of the reverse of the device of FIG. 1.

Referring to FIGS. 1-5, a first embodiment of a device for testing the levels of a given analyte present in saliva shown generally as 10 comprises two arms, a first arm 12 and a second arm 14, which are connected at one end via a hinge 15 which allows the two arms to be folded together. Rotation of each of the arms about the hinge is limited to 180°—a fully open, flat device is shown in FIGS. 1 and 2. The two arms are provided at the other end thereof with a clip or releasable lock arrangement, made up of loop 20 on the first arm and projection 21 on the second arm, by means of which the two arms can be locked together.

In relation to the hinge, at the distal end of the first arm 12 is a pad of absorbent material (Capu-cell foam, 3 mm deep) 13 and at the distal end of the second arm 14 is a test strip 16. The area of the pad of absorbent material 13 is about 200 mm$^2$ (20 mm×10 mm) and is larger than the area of the test strip 16, which is about 50 mm$^2$ (10 mm×5 mm), to ensure that the entirety of the test strip 16 is contacted by the pad of absorbent material 13 when the two arms are bought together. Adjacent to the test strip 16 is a colour calibration icon 17. On the reverse side of the second arm 14 is a transparent window 18 through which both the test strip 16 and the colour calibration icon 17 are visible.

During use of the device, a user places the pad in his/her mouth for a predetermined period (usually about 30 seconds) to soak the pad with saliva and then both the first arm 12 and the second arm 14 are rotated towards each other by pivoting on the hinge 15 such that the pad of absorbent material 13 makes contact with the test strip 16. Upon alignment of the first arm 12 with the second arm 14 the lock mechanism 20, 21 is engaged allowing the two arms to become locked together pressing the pad of absorbent material 13 onto the test strip 16. Through window 18, test strip 16 is visible and the colour change generated by the reaction of saliva with reagents in the strip can be seen, recorded and converted to a concentration.

Figures 3, 4, 5:
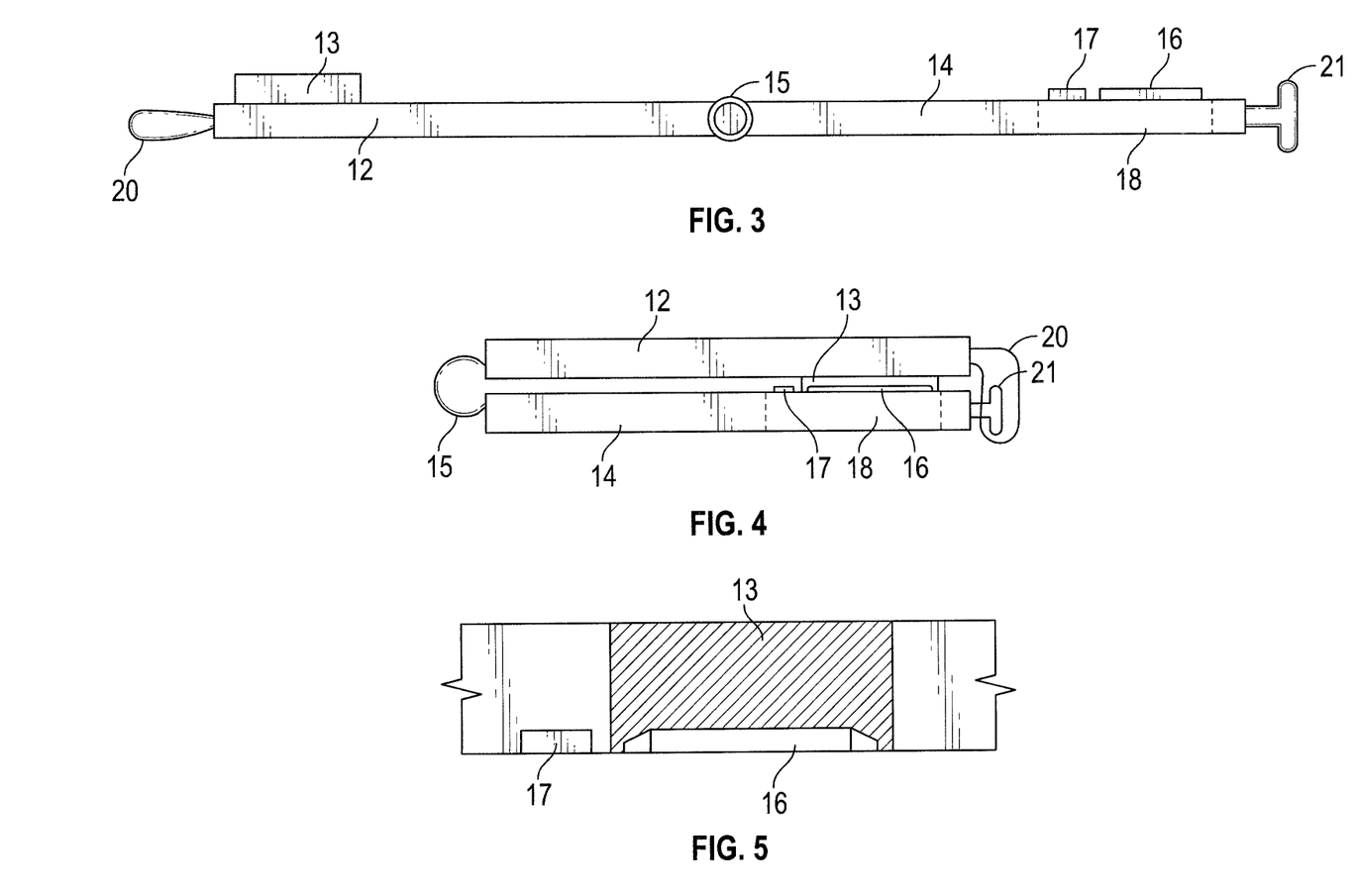
FIG. 3 is a schematic view of the side of the device of FIG. 1.
FIG. 4 is a schematic view of the device of FIG. 1 in a closed position.
FIG. 5 is a schematic, zoomed-in view of the interaction between the pad and the test strip when the device of FIG. 1 is in a closed position.

In FIG. 3 the side of the device is shown when the device is flat in an elongated open position. In this position, the depth of the pad of absorbent material 13 on the first arm 12 is shown and is about 3 mm, and can be compared to the depth of the test strip (drawings not to scale) 16 on the second arm 14, which is about 0.15 mm. The end of the hinge 15 which is approximately positioned in the middle of the device 10 is visible. The test strip 16 can be seen from the rear through the transparent window 18. Shown at opposing ends of the device are components of the lock mechanism, 20 on the first arm and 21 on the second arm.

In FIG. 4 the device 10 is shown in a closed position. First arm 12 and second arm 14 are arranged in parallel such that the pad of absorbent material 13 on first arm 12 is in direct contact with the test strip 16 on the second arm 14. The lock mechanism of the first and second arm 20 and 21 respectively is engaged such that the arms remain locked together with the pad of absorbent material 13 pressed against the test strip 16.

In FIG. 5 more detail of the interaction between the absorbent pad 13 on the first arm 12 and the test strip 16 on the second arm 14 can be seen. The absorbent pad 13 on the first arm 12 contacts the entirety of the test strip 16 on the second arm 14 and contacts a region of the face of the second arm surrounding the test strip. The colour calibration icon 17 can be seen on the second arm 14 adjacent to the test strip 16.

Figure 6:
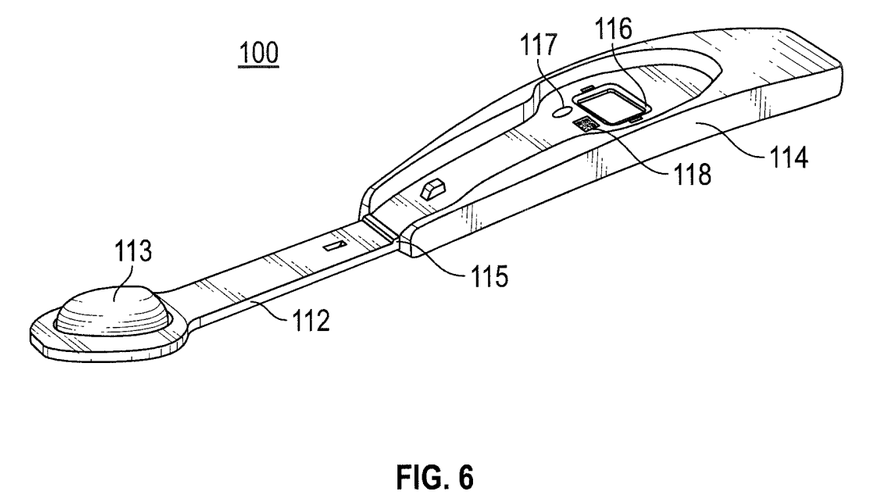
FIG. 6 is a schematic view of the front of a second device of the invention.
Figure 7:
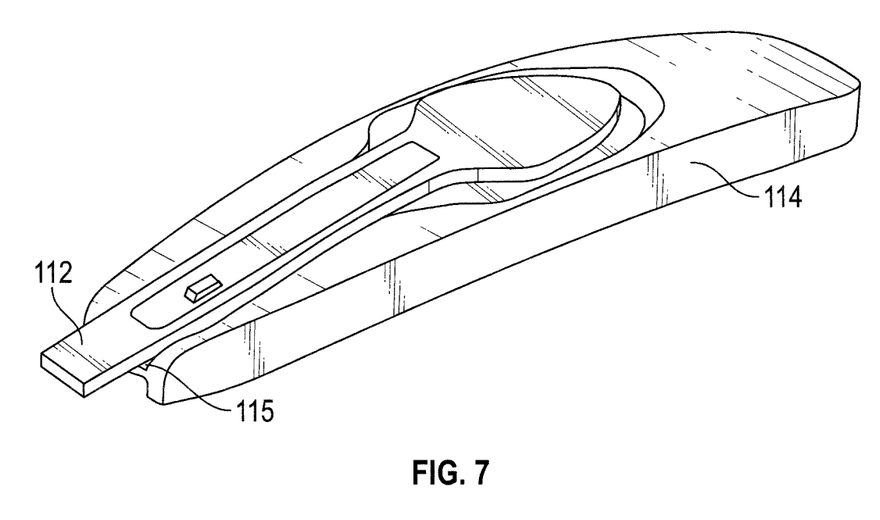
FIG. 7 is a schematic view of the device of FIG. 6 in a closed position.
Figure 8:
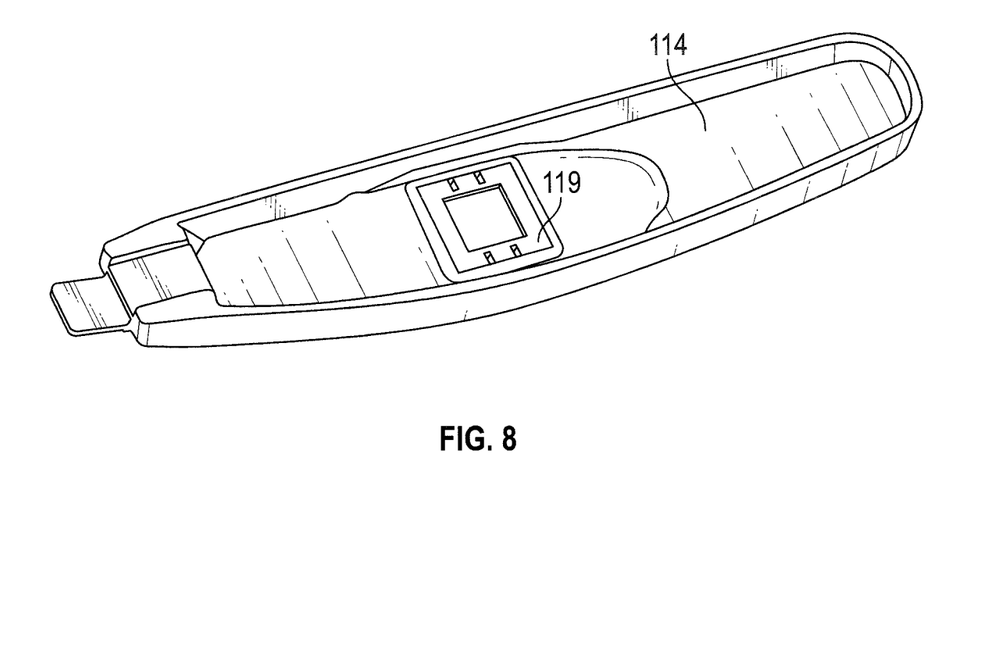
FIG. 8 is a schematic view of the reverse of the second arm of the device of FIG. 6 bearing the test strip.

Referring to FIGS. 6-8, a second embodiment of a device of the invention, shown generally as 100, comprises two asymmetrical arms, a first arm 112 and a second arm 114, which are connected at one end via a hinge 115 which allows the two arms to be folded together. Rotation of each of the arms about the hinge is limited to 180°—a fully open, flat device is shown in FIG. 6.

In relation to the hinge, at the distal end of the first arm 112 is a pad of absorbent material (PureSorb™ Foam Wiper) 113 which has an area of about 200-300 mm$^2$. In the middle of the second arm 114 is a shallow channel 116 for the test strip (not shown) containing the reagent portion. FIG. 8 shows the cassette 119 in which the test strip is comprised and illustrates how the test strip is attached to the reverse of the second arm i.e. by means of a clip. Adjacent to the shallow channel 116 in which the test strip resides is a colour calibration icon i.e. a CMYK icon 117 and a user-identifier i.e. a QR code 118. The area of the channel 116 is dictated by the size of the test strip, which is about 100 mm$^2$ (10 mm×10 mm).

During use of the device 100, a user places the pad 113 in his/her mouth for a predetermined period (usually about 30 seconds) to soak the pad with saliva and then both the first arm 112 and the second arm 114 are rotated towards each other by pivoting on the hinge 115 such that the pad of absorbent material 113 makes contact with the test strip. The two arms are held together by finger pressure for a predetermined period (say 3-5 seconds) before the device is opened by rotating the first arm 112 and the second arm 114 away from each other by pivoting on the hinge 115. In this position the test strip is visible and the colour change generated by the reaction of saliva with the reagents in the test strip can be seen, recorded and converted into a concentration.

Figure 9:
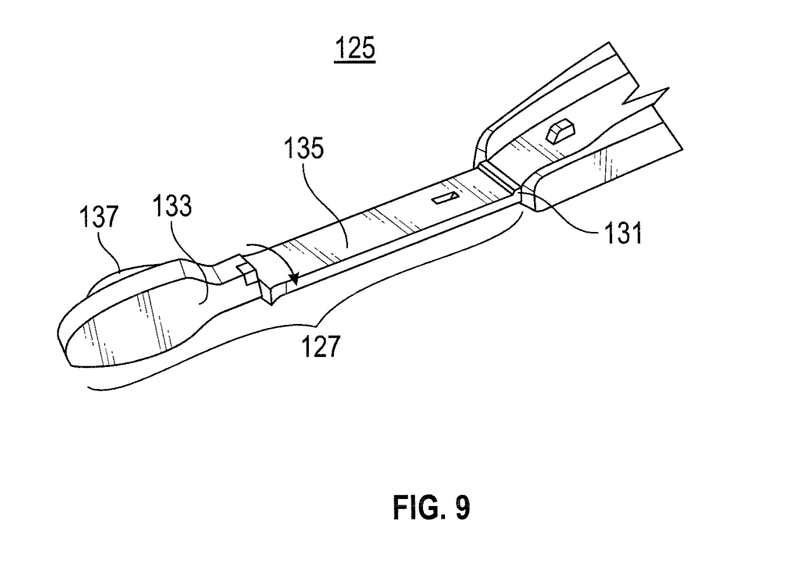
FIG. 9 is a schematic view of the first arm of a third device of the invention.
Figure 10:
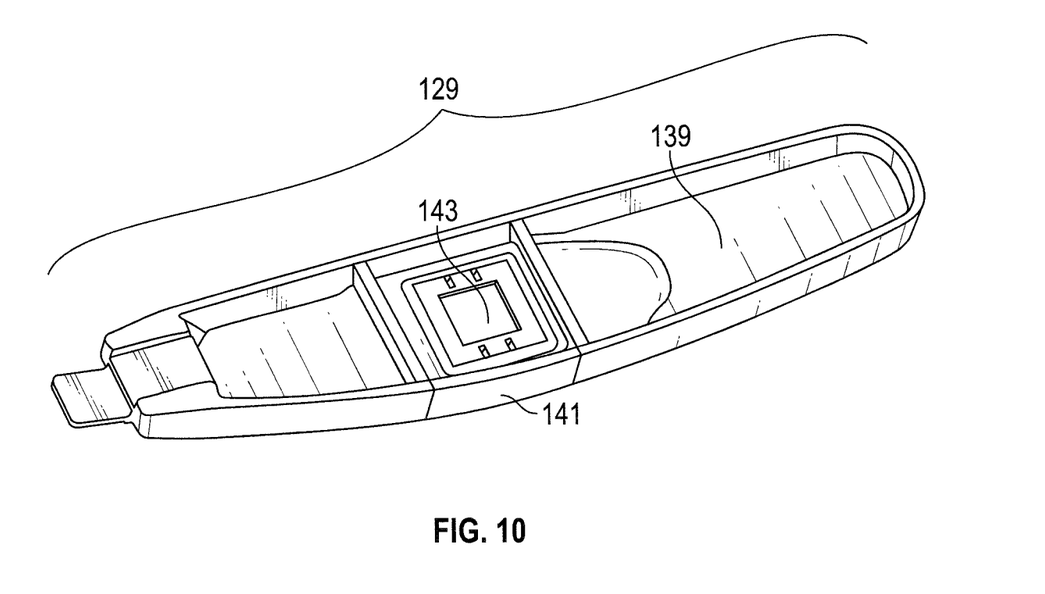
FIG. 10 is a schematic view of the reverse of the second arm of the device of FIG. 9.

FIGS. 9-10 show two halves of a device comprising a third embodiment of the invention. The device comprises two asymmetrical arms, a first arm 127 (FIG. 9) and a second arm 129 (FIG. 10), which are connected at one end via a hinge 131 which allows the two arms to be folded together. FIG. 9 shows the front of the first arm 127 whereas FIG. 10 shows the reverse of the second arm 129.

The first arm 127 contains a detachable head portion 133 and a stem portion 135. The head portion 133 comprises a pad of absorbent material (PureSorb™ Foam Wiper) 137 which has an area of about 200-300 mm². The second arm 129 comprises a main body portion 139 and a releasable cassette 141 comprising a test strip 143. The test strip is accessible from the front surface of the second arm 129.

During use of the device, a user attaches a new head portion 133 containing a pad of absorbent material to the stem portion 135 of the first arm 127. A new cassette 141 is also attached to the main body 139 of the second arm 129. At that point, a user places the pad 137 in his/her mouth for a pre-determined period (usually 30 seconds) to soak the pad with saliva and then both the first arm 127 and the second arm 129 are rotated towards each other by pivoting on the hinge 131 such that the pad of absorbent material 137 makes contact with the test strip. The two arms are held together by finger pressure for a predetermined period (e.g. 3-5 seconds) before the device is opened by rotating the first arm 127 and the second arm 129 away from each other by pivoting on the hinge 131. In this position the test strip is visible and the colour change generated by the reaction of saliva with the reagents in the strip can be seen, recorded and converted into a concentration.

Digital Image Capture and Transmission

Figure 11:
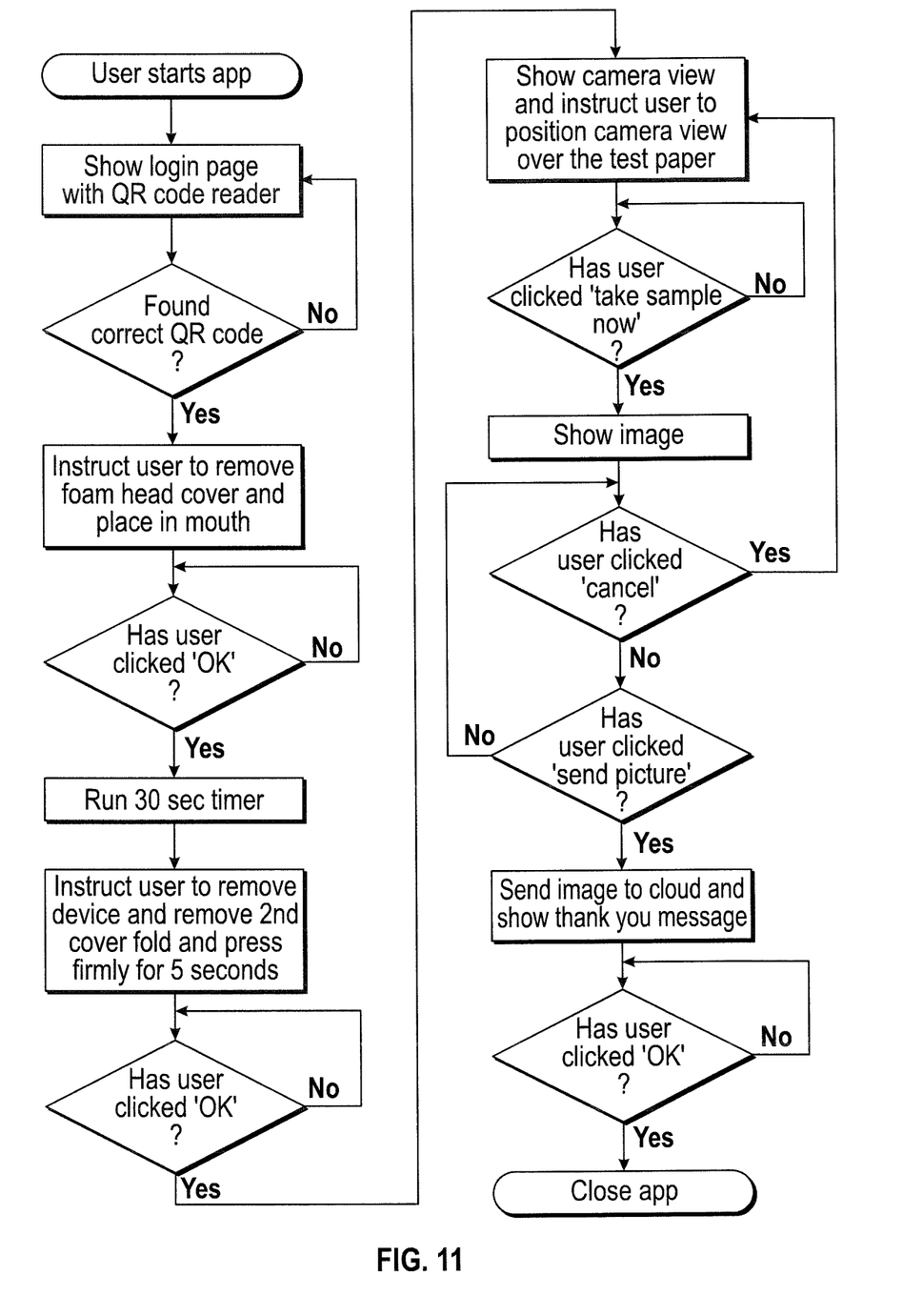
FIG. 11 is a decision tree showing the steps involved in the digital image capture and transmission process i.e. the steps completed by an app run on the smartphone of a user.

FIG. 11 shows the design tree for an app run on the user's smartphone which controls digital image capture and transmission to the monitoring station.

In the first step the user opens the app on her/his smartphone. The app then instructs the user to place the camera over the user-identifier (118 in FIG. 6), so that the inbuilt QR code reader within the app can read the QR code. If the QR code is suitably read then the user progresses to the next step. The user places the foam pad (labelled 113 in FIG. 6) in her/his mouth. Once the user has done so, the user starts the timer on the app which will tell the user when to remove the pad. Once the pad has been removed, the cover is removed from the test strip and the two arms of the device are rotated towards each other so that the pad comes into contact with the test strip. Once the pad is in contact with the test strip the user starts the timer on the app which tells the user when to re-open the device i.e. when to rotate the two arms of the device away from each other such that the test strip is visible. At that point, the app instructs the user to position the camera view over the test paper, the colour calibration icon and the user-identifier i.e. the QR code and take a photograph=digital image. Once the digital image is displayed, the app instructs the user to press send. Once the user presses send, the photograph=digital image showing the test strip, the colour calibration icon and the user-identifier, along with the date and time, is transmitted to a remote monitoring station where the colour information in the photograph is converted into an analyte concentration.

Digital Image Processing and Conversion to Concentration

Figure 12:
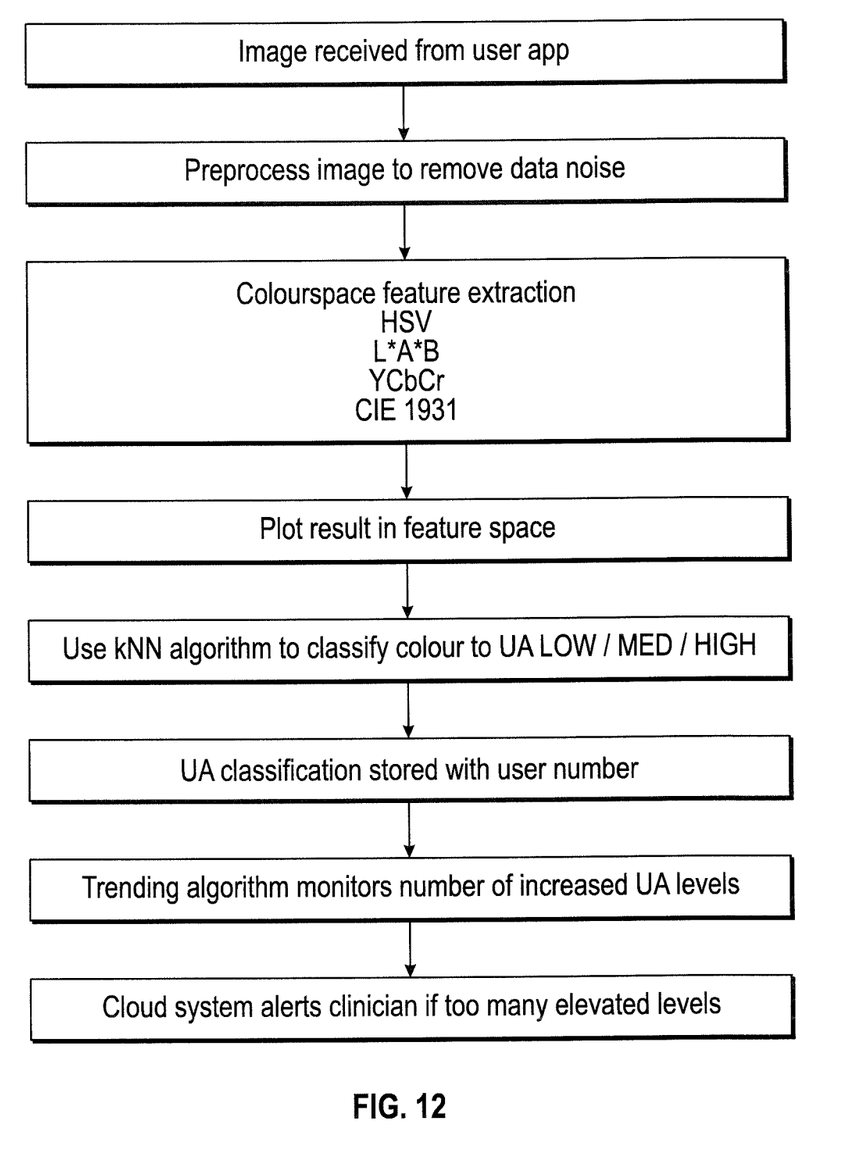
FIG. 12 is a decision tree showing the steps involved in the processing of the digital image of the coloured reagent in the test strip.

FIG. 12 shows the steps involved in processing the digital image to convert the colour information contained within the test strip portion of the digital image into an analyte concentration. These steps are carried out at a remote monitoring station. Instep 1 the remote monitoring station receives the composite image comprising the reagent image data, the calibration data and the user identification details, associated also with a date and time stamp, from the user's smartphone. At this stage the user is identified only by means of the QR code, no personal information is transmitted. Thus the digital image is sent confidentially. In the second step the pre-processing of the digital image is to remove data noise. In the third step colour space feature extraction occurs. Various colour models can be used including HSV (Hue, Saturation, Value), L*A*B (Luminance (L) and two colour channels (a & b), YCbCr (Luma component (Y) and chrominance-blue (Cb) and chrominance red (Cr)) and CIE 1931. In the fourth step the result is plotted from the colour space feature extraction in a feature space plot already populated with data points indicating low, medium or high uric acid levels. The data points were obtained in a prior clinical trial and the low, medium, high categories agreed by a clinician. In the fifth step the k-nearest neighbors algorithm (k-NN) is used to classify the sample as high uric acid/medium uric acid or low uric acid. Once the sample has been classified, the result is stored alongside the user-identifier and the date and time. A trending algorithm monitors for instances of increased uric acid levels. Should an instance arise, the monitoring platform alerts the clinician who can link the user-identifier with a patient.

Example 1

Protocol: Monitoring of Salivary Urate and Use in Diagnosis

The above described second embodiment of the device of the invention is used in combination with the above described app and monitoring station platform.

Enrolment

A pregnant woman enrolls into the monitoring and diagnosis programme. She is allocated unique identification details, encoded in a QR code that is attached to her notes at the hospital and to the device that she is given.

Sample Taking

The pregnant woman (referred to as the user) places the sponge-containing end of the device of FIGS. 6-8 into her mouth for approximately 30 seconds.

The user then removes the sponge from her mouth, folds the device about the hinge and presses the sponge containing end, now wet with saliva, onto the test strip for approximately 3-5 seconds.

Capture of Test Image and Calibration Image

The user reopens the hinge after 3-5 seconds, revealing the test strip that has now to a greater or lesser extent reacted with urate in the saliva in the sponge, generating a colour change of the reagent in the test strip.

Via an app run on the user's smartphone, the user takes a digital photograph (=digital image) of the test strip, including in the photograph the colour calibration icon and the QR code which are adjacent to the test strip. These provide colour calibration and patient identification details in the form of a number.

The user transmits, by pressing send on the app, to a remote monitoring station the digital image comprising a digital image of the coloured reagent, a digital image of the colour calibration icon and a digital image of the QR code.

Processing of Image Data

The remote monitoring station receives the composite image comprising the reagent image data, the calibration data and the user identification details, associated also with a date and time stamp.

If this is the first data received for that user, then a new set of records is generated.

If there is an existing set of records for that user, then the data is added to the set.

The image data is processed by colour space feature extraction and plotted on a feature space plot. A K-NN algorithm is then used to classify the colour content of the reagent image as "low", "medium" or "high" uric acid level.

If a user generates a single "high" reading, an alert is generated.

If the "high" reading is generated after three or more "low" readings, then a "one-off" alert is generated.

If the user generates a "high", preceded by two or more "medium" readings in the previous three weeks, then a "trending high" alert is generated.

The alert is transmitted to the hospital; only there can combining the QR code and hospital records identify the user who can be contacted by the appropriate staff member e.g. mid-wife, clinician etc.

Reminders

The user is sent a reminder to carry out another test once every week during the monitoring period.

The monitoring period beings at week 20 of pregnancy and continues until term.

Accordingly, the invention provides methods for testing for an analyte in an individual and devices for use therein.

The invention claimed is:

1. A method of testing for an analyte in an individual, comprising:
   providing color information obtained from a digital image of a colored reagent on an analyte test strip, the colored reagent having been generated in accordance with analyte in a test sample;
   converting the color information from the digital image into an analyte level;
   recording the analyte level in association with user-specific information, wherein the digital image comprises user specific information;
   repeating the above steps to obtain two or more records of analyte levels for the same user at different times; and
   using the records to monitor personal health or to predict the likely development of a disease or condition or to diagnose a disease or condition or to monitor a treatment regime associated with variation in analyte levels in saliva; and
   further comprising a preliminary step of capturing the digital image of the colored reagent on the analyte test strip at a first site; and
   transmitting the digital image to a monitoring station at a second, remote site, where the color information from the image is converted into the analyte level.

2. The method according to claim 1, wherein the digital image comprises a color reference.

3. The method according to claim 1, wherein converting the color information from the digital image into an analyte level comprises:
   comparing color information from the digital image with color information obtained from images generated during a clinical trial, wherein the color information obtained from images generated during the clinical trial has been linked to levels of a given analyte.

4. The method according to claim 1, further comprising processing the digital image to obtain the color information from the digital image.

5. The method according to claim 1, further comprising determining the analyte level based upon luminance, saturation, or both luminance and saturation of the color.

6. The method according to claim 3, comprising using the comparison to identify incidence of high urate levels.

7. The method according to claim 1 is used for diagnosis of fetal stress.

8. The method according to claim 1 is used for diagnosis of risk of pre-eclampsia.

9. A method of testing for an analyte in an individual, comprising:
   (a) providing (i) a saliva sample from an individual in a pad of absorbent material, spaced from (ii) a test strip containing an indicator which is capable of generating a color change in accordance with the presence of an analyte;
   (b) bringing the pad into contact with the test strip and holding the pad in contact with the test strip for sufficient time for saliva in the pad to be combined with the indicator and generate a color in accordance with a level of an analyte if present; and
   (c) determining the level of analyte based upon the color change;
   wherein step (c) comprises transmitting information concerning the level of an analyte to a monitoring station at a remote site; and
   wherein the information transmitted comprises color information contained in or obtained from an image of the color on the test strip, and
   further comprising
   storing at least 5 test results for the same user taken at different times; and
   comparing these test results to monitor personal health or predict the likely development of a disease or condition or diagnose a disease or condition or to monitor a treatment regime associated with variation in analyte levels in saliva.

10. The method according to claim 9, wherein the indicator is capable of generating a color change in accordance with the concentration of an analyte.

11. The method according to claim 9, wherein the method comprises determining the analyte level based upon luminance, saturation, or both luminance and saturation of the color.

12. The method according to claim 9, comprising comparing test results to identify incidence of high urate levels.

13. The method according to claim 9, comprising carrying out the test using a device comprising:
   (a) a first arm, on which is mounted a pad of absorbent material; and
   (b) a second arm, comprising a test strip, wherein the test strip comprises a reagent portion comprising the indicator capable of generating a color change in accordance with the presence of an analyte;
   wherein the arms are connected by a hinge and can be pivoted on the hinge to bring the pad into contact with the reagent portion; and
   wherein the second arm additionally comprises a color calibration icon.

14. The method according to claim 13, wherein the second arm comprises a user identifier.

15. The method according to claim 9 is used for diagnosis of fetal stress.

16. The method according to claim 9 is used for diagnosis of pre-eclampsia.

* * * * *

UNITED STATES PATENT AND TRADEMARK OFFICE
CERTIFICATE OF CORRECTION

| | | |
|---|---|---|
| PATENT NO. | : 11,193,892 B2 | Page 1 of 1 |
| APPLICATION NO. | : 16/093526 | |
| DATED | : December 7, 2021 | |
| INVENTOR(S) | : Susan Elizabeth Clarke et al. | |

It is certified that error appears in the above-identified patent and that said Letters Patent is hereby corrected as shown below:

On the Title Page

Item (30), under "Foreign Application Priority Data," "1606549" should read --1606549.2--.

Signed and Sealed this
Seventeenth Day of May, 2022

Katherine Kelly Vidal
*Director of the United States Patent and Trademark Office*